(12) United States Patent
Sheikh

(10) Patent No.: US 6,589,272 B1
(45) Date of Patent: Jul. 8, 2003

(54) THERMAL PACK RETAINING APPARATUS

(76) Inventor: Shahid Sheikh, 1238 10th St. #10, Santa Monica, CA (US) 90401

( * ) Notice: Subject to any disclaimer, the term of this patent is extended or adjusted under 35 U.S.C. 154(b) by 0 days.

(21) Appl. No.: 09/488,481

(22) Filed: Jan. 20, 2000

Related U.S. Application Data

(60) Provisional application No. 60/116,481, filed on Jan. 20, 1999.

(51) Int. Cl.[7] .................................................. A61F 7/00
(52) U.S. Cl. ...................................... 607/108; 607/112
(58) Field of Search ................................ 607/108, 112; 602/2, 14

(56) References Cited

U.S. PATENT DOCUMENTS

| | | | | |
|---|---|---|---|---|
| 1,488,743 A | * | 4/1924 | Eggers | |
| 3,900,035 A | * | 8/1975 | Welch et al. | 128/402 |
| 4,190,054 A | * | 2/1980 | Brennan | 128/402 |
| 4,527,566 A | * | 7/1985 | Abare | 128/402 |
| 4,688,572 A | * | 8/1987 | Hubbard et al. | 128/402 |
| 4,706,673 A | * | 11/1987 | Meistrell | 128/402 |
| 4,976,262 A | * | 12/1990 | Palmacci | 128/402 |
| 5,111,810 A | * | 5/1992 | Fortney | 128/402 |
| 5,148,804 A | * | 9/1992 | Hill et al. | 128/402 |
| 5,728,058 A | * | 3/1998 | Ouellette et al. | 602/62 |
| 5,823,984 A | * | 10/1998 | Silverberg | 602/61 |
| 5,860,945 A | * | 1/1999 | Cramer et al. | 602/62 |

* cited by examiner

*Primary Examiner*—Linda C. M. Dvorak
*Assistant Examiner*—Jocelyn D Ram
(74) *Attorney, Agent, or Firm*—Marshall E. Rosenberg

(57) ABSTRACT

A joint-specific apparatus that reliably retains a cold pack in a preselected position and under compression adjacent to an anatomical structure such as a limb or joint, or adjacent to an anatomical region, to maximize the desired therapeutic effect when that anatomical structure or region is cooled or heated.

21 Claims, 3 Drawing Sheets

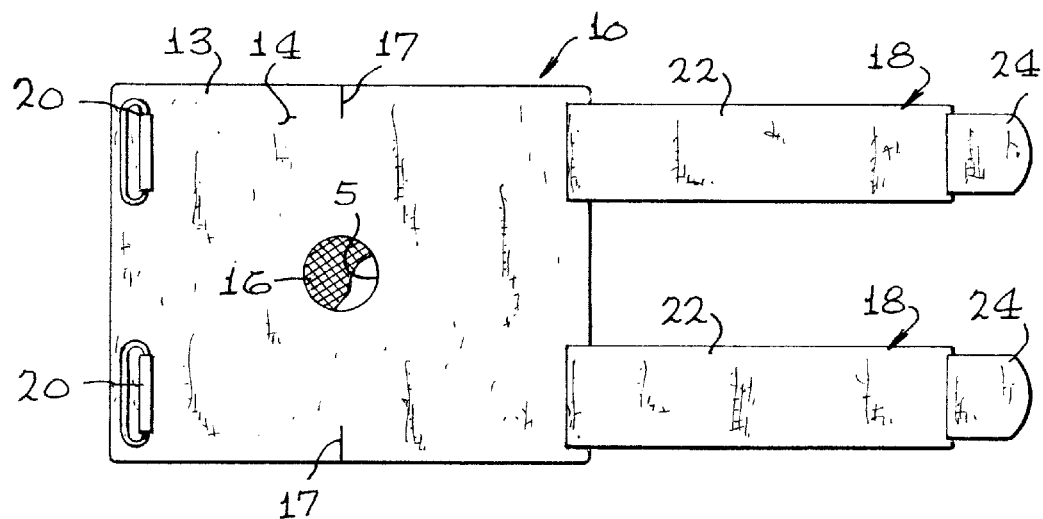
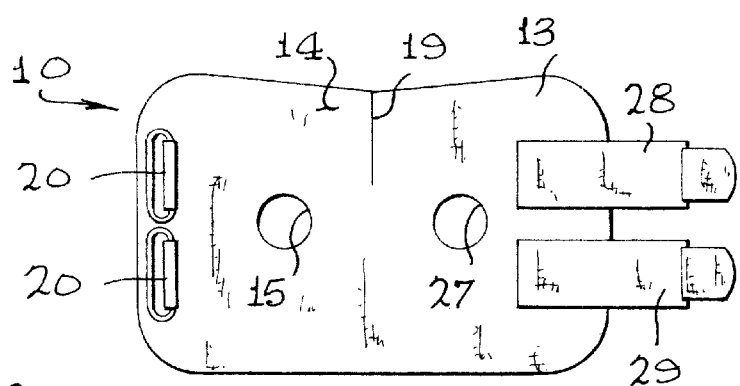
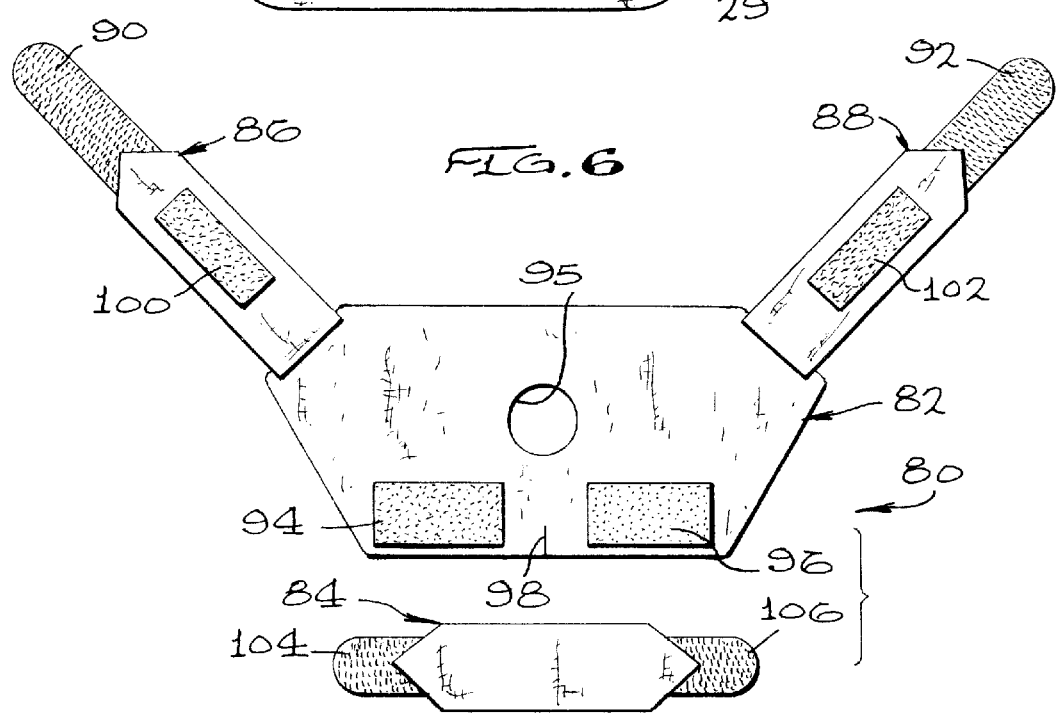

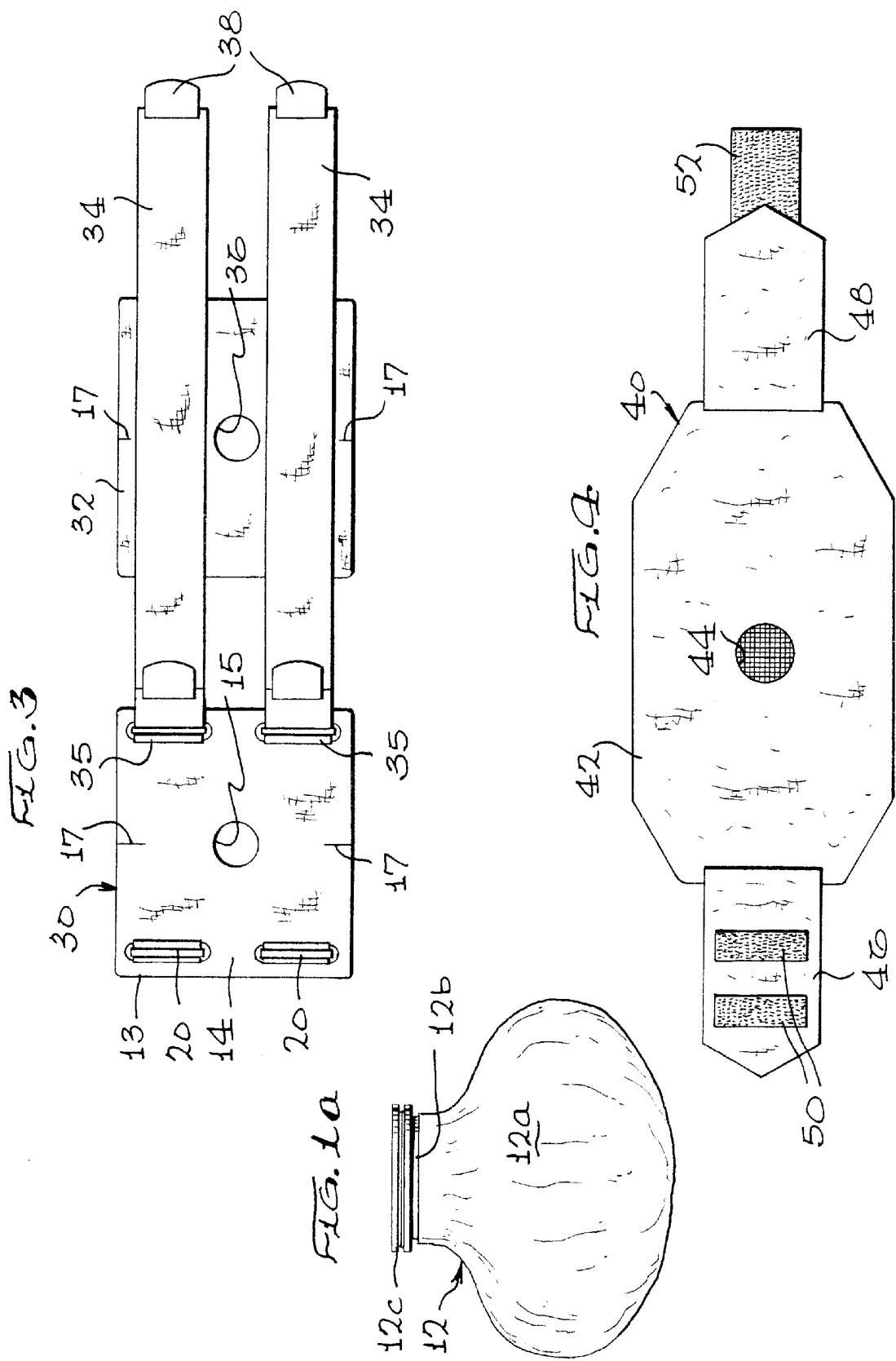

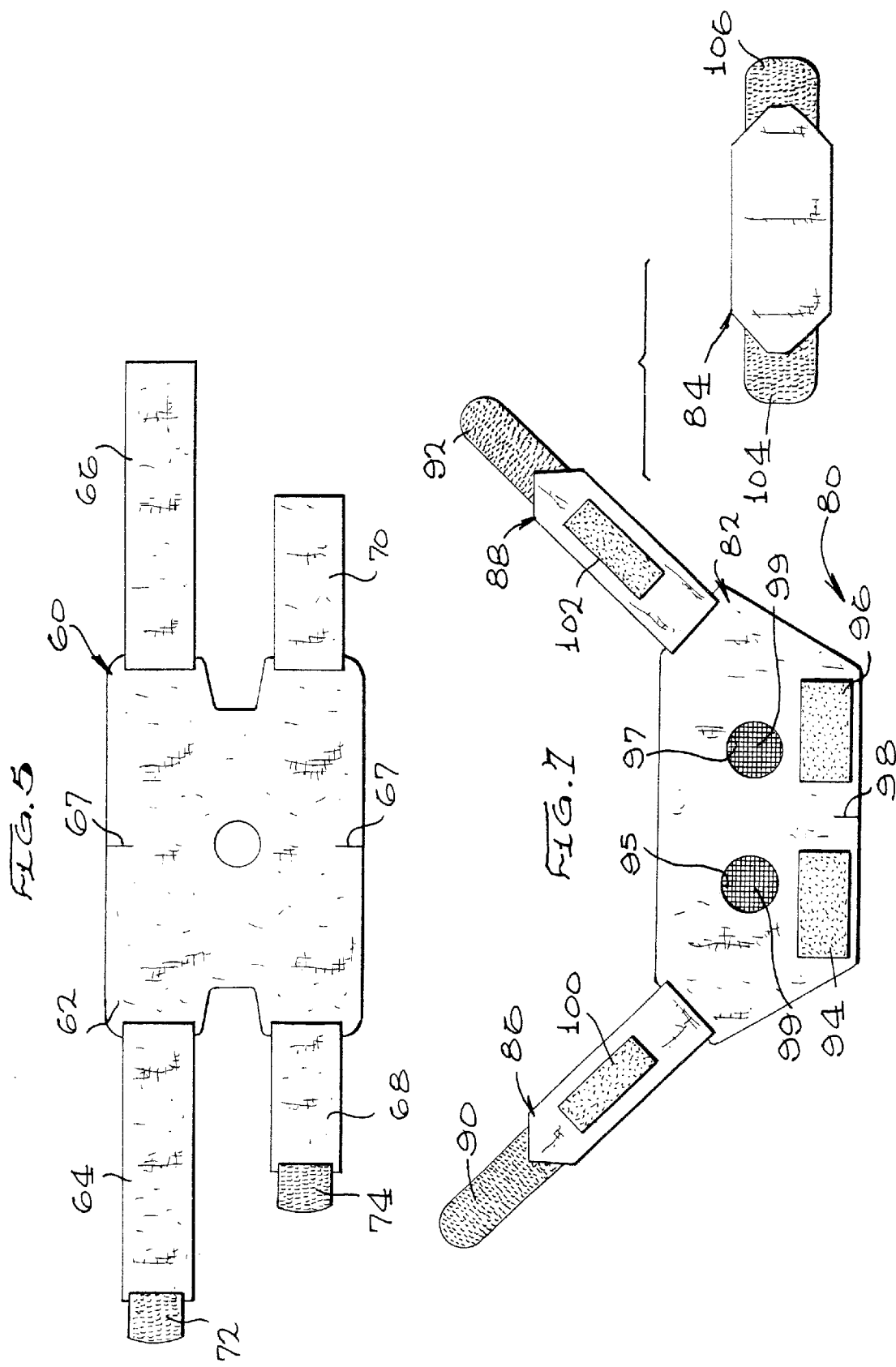

THERMAL PACK RETAINING APPARATUS

CROSS REFERENCE TO RELATED APPLICATIONS

This application claims the benefit of U.S. Provisional Application No. 60/116,481, filed Jan. 20, 1999.

FIELD OF THE INVENTION

The present invention relates generally to the field of treatment for sports/medical injuries, and more specifically, to apparatus for selectively applying a hot/cold pack to the human anatomy and reliably retaining the hot/cold pack in position to maximize the desired therapeutic effect.

DESCRIPTION OF THE RELATED ART

"Hot" or "cold" packs (hereinafter referred generically as "cold packs") are well known and widely used to heat or cool injured body parts of the human anatomy as necessary to accelerate healing. More particularly, cold packs are conventionally employed for providing thermal therapeutic value to assist in healing of injuries suffered during exercise, sports or on-the-job activities, accidents, and under circumstances in which a muscle, ligament or tendon is sprained, torn or otherwise traumatized. Cold packs may also be applied, following a surgery or during physical rehabilitation, adjacent to the affected anatomical structure, to assist in healing of the affected body part.

However, under any of these circumstances, the prior art has attempted, but has insufficiently provided, an apparatus that reliably secures and retains an ice pack in a preselected position to maximize the desired therapeutic effect. For example, U.S. Pat. No. 4,585,003 to Meistrell discloses an ice-pack.retention device that includes two generally parallel, elongated legs for securing the ice pack to a limb or the like. However, the retention device of Meistrell fails to securely retain the ice pack in position due to the inherent instability of that design which allows for translational and rotational slippage along the limb, due in part to undesired stretchability of the flexible elongated legs.

SUMMARY OF THE INVENTION

The present invention is a joint-specific apparatus that reliably retains one or more cold packs in a preselected position adjacent an anatomical structure such as a limb or joint, or adjacent to an anatomical region, to maximize the desired therapeutic effect when that anatomical structure or region is cooled or heated. The apparatus in its various embodiments may be applied to the shoulder, elbow, wrist, back, hip, knee or ankle and simultaneously provides heating/cooling therapy in combination with a desired level of compression to the affected joint or region.

BRIEF DESCRIPTION OF THE DRAWINGS

FIG. 1 is a top plan view showing a first embodiment of the present invention.

FIG. 1a is a perspective view of a cold pack for use with any of the embodiments of the present invention.

FIG. 2 is a top plan view showing a second embodiment of the present invention.

FIG. 3 is a top plan view showing a third embodiment of the present invention.

FIG. 4 is a top plan view showing a fourth embodiment of the present invention.

FIG. 5 is a top plan view showing a fifth embodiment of the present invention.

FIG. 6 is a top plan view showing a sixth embodiment of the present invention.

FIG. 7 is a top plan view showing a seventh embodiment of the present invention.

DETAILED DESCRIPTION

With reference now to the drawings, according to the first embodiment of the present invention, FIG. 1 shows an apparatus 10 for retaining a cold pack 12 (FIG. 1a), the assembly to be secured to a preselected anatomical structure or region of the human anatomy, such that apparatus is joint-specific as will be more fully described below. It will be understood that the term "cold pack" includes without limitation ice packs, heating packs, water bags for receiving ice, ice water, chilled or heated water or other thermal mixtures or solutions that radiate heat or cold, and when retained by apparatus 10, provide the desired therapeutic effect to the selected anatomical structure or region. It will be further understood that the cold pack 12 may use natural or synthetic materials to provide the desired heating or cooling effect.

Again referring to FIG. 1, apparatus 10 includes a body portion 13 having a top face 14 formed from a sheet material such as neoprene or other material offering good resiliency characteristics. Preferably, body portion 13 is a laminate of neoprene with an underside lining of wear-resistant nylon. Alternatively, a laminate of nylon/neoprene/nylon may be used. According to any of these constructions, a hole 5 formed in top face 14 is sized to retain a cold pack, such as a water bottle 12 having a bladder 12a secured to neck 12b which is terminated by a removable cap 12c. In the installed condition, bladder 12a is projected through the top face 14 so that neck 12b is retained within hole 5 and bladder 12a is positioned against the inner side of top face 14 for direct application against the selected anatomical region to be treated. Optionally, an inner layer 16 such as an elastic mesh material layer (partially shown by cross-hatching within hole 5) is secured to an extent of the inner side of top face 14 to form a pocket in cooperation with the inner side of top face 14 within which bladder 12a is received and supported. The inner layer 16 is sufficiently thin and/or porous so as not to significantly impede heat/cold transfer between the cold pack and the user's skin. The body portion 13 is generally rectangular although other shapes including square and round body portions are contemplated by the present invention to accommodate and conform to a particular anatomical structure. To further improve conformation to the particular anatomical structure and to better support the cold pack 12, portions of the body portion 13 are gathered at seams 17.

Two generally flat straps 18 each having a main portion 22 terminated by a tab 24 are affixed adjacent to a first edge of the body portion 13, and two buckles 20 sized to receives the straps 18 are affixed to a second edge of the body portion 13 opposite the first edge to secure the apparatus 10 around an anatomical structure. Alternatively, the apparatus 10 is secured in position by providing a hook fabric of a hook-and-loop fastener on tab 24 (or fabricating tab 24 exclusively of the hook fabric) and affixing it to a corresponding loop fabric provided on main portion 22 (or fabricating main portion 22 exclusively of the loop fabric). Top face 14 may include a hook-and-loop fastener component or layer to receive a section of the fastener straps. Preferably, the loop fabric is a non-pile loop fabric to minimize or eliminate fraying. Because secure retention characteristics are important to the successful application of the apparatus 10, the selected sheet material of the body portion 13 has elastic properties. Likewise, straps 18 are comprised of a material having either no stretch or controllable stretch characteristics in the lateral direction, i.e., along the length of the straps 18, such that overall dimensions and correlated tightness/looseness of the in situ apparatus is provided exclusively by adjustment of one or both straps 18, thereby overcoming an important deficiency (uncontrolled stretch) in the related art. As another important benefit, a preselected level of compression is simultaneously applied, thereby providing a synergistic application of a controllable level of compression in conjunction with heat/cool therapy.

To apply apparatus 10, the cold pack 12 is secured in the manner described above, with the cold pack 12 applied directly or indirectly to the anatomical region to be treated. Each strap 18 is wrapped about the appropriate anchoring body part and passed through the opposing corresponding buckle 20 and anchored by folding and doubling back through the buckle 20. The strap 18 is then cinched to an appropriate tension and tab 24 is pressed down onto the back portion of the strap to engage the hook-and-loop fastener, thereby securing the assembly of the apparatus 10 and cold pack 12 in place, and providing thermal treatment under controllable compression conditions.

The apparatus is joint specific, such that apparatus 10 may be sized and modified to accommodate different anatomical parts. For example, a larger size embodiment of the apparatus 10 may be applied to the knee, thigh or groin for hamstring pulls, thigh contusions or to accommodate a larger knee size. A medium size embodiment of the apparatus 10 may be applied to an average knee, ankle or shin for control of common muscle and joint pair and swelling from tendinitis, bursitis, sprains or strains. Furthermore, the medium size embodiment may be used by runners or joggers suffering from shin splints or stress fractures. A small size embodiment of the apparatus may be applied to the elbow or wrist to treat tennis elbow or carpal tunnel syndrome.

FIG. 2 shows a second embodiment of the invention, which is a modification of apparatus 10, further including a second hole 27 for securing a second cold pack 12 to an ankle or other anatomical structure or region in the manner previously described. More particularly, two cold packs 12 may be simultaneously retained by apparatus 10 in holes 5, 27 provided in spaced arrangement along a lateral extent of top face 14 to provide bilateral coverage and a customized fit for treatment of an injured ankle. In use, one strap 28 is wrapped around the user's ankle, and the other strap 29 is wrapped around the bottom of the user's foot to position and secure the cold packs 12 on opposite sides of the ankle when the apparatus 10 is cinched and secured in the manner previously described. Also, it will be appreciated that a single cold pack 12 may be used in either hole 5,27 as desired. The body portion 13 may be gathered at seam 19 to form a shallow concavity or pocket to better conform the apparatus 10 to the user's ankle.

FIG. 3 shows a third embodiment of the present invention, and a modification of apparatus 10 shown in FIG. 1, for providing bilateral heat/cold coverage to the knee or ankle. More particularly, apparatus 30 further includes an intermediate body portion 32 supported at an intermediate lateral extent of a pair of substantially parallel straps 34. The intermediate body portion 32 may be removably secured to the straps 34 by cooperating hook-and-loop fabric engagement panels attached to the intermediate body portion 32 and straps 34 or by sewing or other permanent attachment means. One end of each strap 34 is secured to the body portion 13 by buckles 35 similar to buckles 20. Tabs 38 similar to tabs 24 are provided on the free ends of straps 34. A hole 36 is sized and shaped in a manner identical or similar to hole 5 to retain a second cold pack 12 in the manner previously described.

In use, one strap 34 is wrapped around the user's leg above the knee; and the other strap 34 is wrapped around the user's leg below the knee to position and secure the cold packs 12 on opposite sides of the knee when the apparatus 30 is cinched and secured at both sets of buckles 20, 35 in the manner previously described. Also, it will be appreciated that a single cold pack 12 may be used in either hole 5,36 as desired. In the installed condition, apparatus 30 is suitable for post surgical use, rehabilitation and maintenance of anterior/posterior cruciate ligament repair, by substantially surrounding the entire knee with cold (with ice pack usage) and compression for control of pain and swelling. As previously described, a mesh inner layer similar to inner layer 16 may be used to further secure the cold pack(s) 12 in place.

FIG. 4 shows a fourth embodiment of the present invention, for use on the user's back. More particularly, apparatus 40 includes a back strap 42 similar to body portion 13 having a hole 44 for receiving and retaining a cold pack 12 in the manner previously described. Two securing straps 46,48 are secured at opposite lateral ends of back strap 42. Two panels 50 of a loop fabric of a hook-and-loop fastener are secured to securing strap 46, and a corresponding panel 52 of a hook fabric is attached to the outer lateral edge of securing strap 48. According to this embodiment, an inner mesh layer of fabric (not shown) may be provided to form a pocket to further secure the cold pack 12 of the size used in the other embodiments of the invention, or a cold pack having a larger bladder to provide broader coverage of the back. Accordingly, apparatus 40, in the installed condition, is useful for treatment of back problems involving spinal discs, muscle spasms and control of post-surgical pain and swelling, using both heat and cold therapy.

FIG. 5 shows a fifth embodiment of the present invention, for use on a user's hip. More particularly, apparatus 60 includes a body portion 62, with an upper set of straps 64, 66 and a lower set of straps 68, 70 extending therefrom. Upper straps 64,66 are optionally longer than lower straps 68,70. Each strap 64,68 includes a tab 72,74, respectively, of a hook fabric of a hook-and-loop fastener, for fastening to a cooperating loop fabric integrally formed with or applied to straps 66,70 in the manner previously described. Optionally, body portion 62 may be molded to a more conforming shape by gathering portions of body portion 62 at seams 67 to form a shallow concavity or pocket within the body portion 62. After cold pack 12 is secured within hole 65 such that bladder 12a extends into the shallow concavity, apparatus 60 is applied to the user's left or right hip by wrapping and securing the upper straps 64,66 about the user's waist, and wrapping and securing the lower straps 68,70 about the user's leg on the side of the injured hip, thereby positioning cold pack 12 in direct proximity to the injured region. In the installed condition, treatment is provided for problems including bursitis and swelling caused by closed fractures and other hip injuries, or to provide relief for the pain and swelling associated with hip replacement surgery.

FIG. 6 shows a sixth embodiment of the present invention, for use on a user's shoulder. More particularly, apparatus 80 includes a main body portion 82 and an elastic strap 84 for use with left or right shoulder applications. Main body portion 82 includes two upper straps 86,88 each extending upwardly at an acute angle relative to the main body portion 82. The straps can extend at about a 45 degree angle, although the apparatus may be provided with lesser or greater angular extensions depending on the size and proportions of the intended user. Upper straps 86,88 includes tabs 90,92, respectively, of a hook fabric of a hook-and-loop fastener, for fastening to opposing patches 100,102 of cooperating loop fabric secured to upper straps 86,88 after the straps are encircled about the user's torso. Elastic strap 84 also includes tabs 104,106 of a hook fabric of a hook-and-loop fastener for encircling the user's upper arm and fastening to patches 94,96 of cooperating loop fabric positioned at lower lateral areas of main body portion 82, thereby reliably capturing the cold pack 12 retained in hole 95 in the desired position adjacent to the shoulder. Optionally, main body portion 82 may be molded to a shape that more closely conforms to the human shoulder by gathering portions of main body portion 82 at seam 98 to form a shallow concavity or pocket within the body portion 82. In the installed condition, treatment is provided for problems including rotator cuff injuries such as tendonitis, impingement syndrome, bursitis and post surgical pain and swelling.

FIG. 7 shows a seventh embodiment of the invention, which is a modification of apparatus 80 shown in FIG. 6, further including a second hole 97 for securing a second cold pack 12 to a shoulder in the manner previously described. More particularly, two cold packs 12 may be simultaneously retained by apparatus 80 in holes 95,97 provided in spaced arrangement along a lateral extent of main body portion 82 to provide bilateral coverage about the injured shoulder, i.e., one cold pack 12 is positioned adjacent the front of the shoulder and the other cold pack 12 is positioned adjacent the back of the shoulder. It will be appreciated that a single cold pack 12 may be retained in either hole 95,97 as desired to treat a more localized area on the front or back of the shoulder although still adjacent to the shoulder. Optionally, an inner layer 99 such as an elastic mesh material layer (shown by cross-hatching within holes 95 and 97) is secured to an extent of the inner side of main body portion 82 to form a pocket in cooperation with the inner side of main body portion 82 within which bladder 12*a* is received and supported. The inner layer 99 is sufficiently thin and/or porous so as not to significantly impede heat/cold transfer between the cold pack 12 and the user's skin.

It is to be understood that the present invention is not limited to the embodiments described above, but encompasses any and all embodiments within the scope of the following claims.

What is claimed is:

1. Apparatus for positioning and securing for use therewith a thermal source adjacent to a predetermined anatomical region or structure of a user, the thermal source supported within a bladder, the apparatus comprising:
    a main body being configured to generally conform to the contours of the specific anatomical region or structure; and
    at least one positioning strap secured at one end to the main body, the positioning strap being stretchable along a width of the strap, wherein said width is adapted to be coaxial with a longitudinal axis of the anatomical region of the patient and transverse to the bending axis of said anatomical region when the device is in use, an assembly of the main body and the bladder closely conforming to the anatomical region or structure when positioned and secured under compression by the positioning strap extended about the user to simultaneously provide thermal and compressive therapy to the anatomical region or structure.

2. The apparatus of claim 1, further comprising a plurality of positioning straps, each said positioning strap adapted to be adjustably positioned about the user.

3. The apparatus of claim 1, wherein the bladder is secured to a filling port having a neck for receiving the thermal source, and the bladder is secured to the main body having a recess for removably securing the bladder by the neck.

4. The apparatus of claim 3, wherein the filling port is sealably closed with a removable cap securable to the neck adjacent to an outer side of the main body, the so-secured cap anchoring the bladder in position adjacent to the main body.

5. The apparatus of claim 3, wherein the filling port is sealably closed with a removable cap securable to the neck adjacent to an outer side of the main body, the so-secured cap anchoring the bladder in position adjacent to the main body.

6. The apparatus of claim 1, wherein the main body is formed of a resilient sheet material.

7. The apparatus of claim 1, wherein the thermal source radiates heat or cold.

8. The apparatus of claim 7, wherein the thermal source is selected from the group including ice, ice water, chilled water, heated water, and gel packs.

9. Apparatus for positioning and securing for use therewith a thermal source adjacent to a predetermined generally articulable anatomical joint selected from the group including an elbow, knee or ankle, the thermal source supported within a bladder, the apparatus comprising:
    a main body being configured to generally conform to the contours of the joint; and
    a pair of positioning straps each secured at one end to the main body, an assembly of the main body and the bladder generally conforming to the joint when positioned and secured under compression to the user by extending the positioning strap about the user to simultaneously provide thermal and compressive therapy to the joint wherein each positioning strap is stretchable along a width of the strap, wherein said width is adapted to be coaxial with a longitudinal axis of the joint of the patient and transverse to the bending axis of said joint when the device is in use.

10. The apparatus of claim 9, wherein the positioning straps are adapted to be secured about anatomical structures separated by the joint.

11. The apparatus of claim 9, further comprising a pair of bladders supported on opposite sides of the anatomical structure.

12. The apparatus of claim 9, wherein the bladder is secured to a filling port having a neck for receiving the thermal source, and the bladder is secured to the main body having a recess for removably securing the bladder by the neck.

13. The apparatus of claim 9, wherein the main body is formed of a resilient sheet material, and the strap is formed of an essentially non-elastic material for application to a knee.

14. The apparatus of claim 9, wherein the thermal source radiates heat or cold.

15. The apparatus of claim 14, wherein the thermal source is selected from the group including ice, ice water, chilled water, heated water, and gel packs.

16. Apparatus for positioning and securing for use therewith a thermal source adjacent to a right or left human shoulder, the thermal source supported within a bladder, the apparatus comprising:
    a main body shaped to generally conform to the region adjacent to and including the shoulder;
    a first positioning strap secured at one end to an upper lateral portion of the main body, the first positioning strap to be secured about the user's torso, an assembly of the main body and the bladder generally conforming to the shoulder region; and a second positioning strap secured at one end to the lower lateral portion of the main body for securing a lower lateral portion of the main body in encircling engagement with the corresponding upper arm of the user, the apparatus when positioned and secured under compression to the user by the positioning straps simultaneously providing thermal and compressive therapy to the shoulder region wherein each positioning strap is stretchable along a width of the strap, wherein said width is adapted to be coaxial with a longitudinal axis of the shoulder of the patient and transverse to the bending axis of said shoulder when the device is in use.

17. The apparatus of claim 16, further comprising a pair of bladders, one supported adjacent the front of the shoulder and one supported adjacent to the back of the shoulder.

18. The apparatus of claim 16, wherein the second strap is integrally formed at one end with the lower lateral portion of the main body.

19. Apparatus for positioning and securing for use therewith a thermal source adjacent to a right or left side human hip of a patient, said patient having a height, the thermal source; supported within a bladder, the apparatus comprising:

a main body shaped to generally conform to the contours of the hip;

a first positioning strap having an extendible portion secured at one end to an upper lateral portion of the main body, the first positioning strap to be secured about the users waist, an assembly of the main body and the bladder generally conforming to the hip region; and a second positioning strap having an extendable portion for securing a lower lateral portion of the main body in encircling engagement with the corresponding upper leg of the user, the apparatus when positioned and secured under compression to the user by the positioning straps simultaneously providing thermal and compressive therapy to the hip region wherein each positioning strap is elastically stretched along a width of the strap in the heightwise direction.

20. Apparatus for positioning and securing for use therewith a first thermal source adjacent to a knee, the first thermal source supported within a first bladder, the apparatus comprising:

a main body shaped to generally conform to the contours of the knee; and a pair of positioning straps each secured at one end to the main body, an assembly of the main body and the first bladder generally conforming to the joint when positioned and secured under compression to the user by extending the positioning straps about the user's leg to simultaneously provide thermal and compressive therapy to the knee wherein each positioning strap is stretchable along a width of the strap, wherein said width is adapted to be coaxial with a longitudinal axis of the knee of the patient and transverse to the bending axis of said knee when the device is in use.

21. The apparatus of claim 20, further comprising:

an intermediate body portion secured to a lengthwisely intermediate position of at least one of the pair of the positioning straps;

a second thermal source supported within a second bladder, the second bladder supported by the intermediate body portion against the knee in a location opposite the location of the first bladder.

\* \* \* \* \*